US010543320B2

United States Patent
Bernert (10) Patent No.: US 10,543,320 B2
(45) Date of Patent: Jan. 28, 2020

(54) DRIVE ASSEMBLY FOR A DRUG DELIVERY AND DRUG DELIVERY DEVICE

(71) Applicant: Sanofi-Aventis Deutschland GmbH, Frankfurt am Main (DE)

(72) Inventor: Andreas Bernert, Bad Homburg vor de Hohe (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 119 days.

(21) Appl. No.: 14/894,179

(22) PCT Filed: May 13, 2014

(86) PCT No.: PCT/EP2014/059690
§ 371 (c)(1),
(2) Date: Nov. 25, 2015

(87) PCT Pub. No.: WO2014/191190
PCT Pub. Date: Dec. 4, 2014

(65) Prior Publication Data
US 2016/0114108 A1    Apr. 28, 2016

(30) Foreign Application Priority Data
May 27, 2013    (EP) .................................... 13169309

(51) Int. Cl.
*A61M 5/315* (2006.01)
*A61M 5/20* (2006.01)
*A61M 5/48* (2006.01)

(52) U.S. Cl.
CPC .......... *A61M 5/31535* (2013.01); *A61M 5/20* (2013.01); *A61M 5/31551* (2013.01);
(Continued)

(58) Field of Classification Search
CPC ................ A61M 5/31535; A61M 5/20; A61M 5/31551; A61M 5/31553; A61M 5/31583;
(Continued)

(56) References Cited

U.S. PATENT DOCUMENTS

| 533,575   | A | 2/1895 | Wilkens |
| 4,333,359 | A | 6/1982 | Taga et al. |

(Continued)

FOREIGN PATENT DOCUMENTS

| CA | 2138528    |    | 12/1998 |
| CA | 2359375 A1 |    | 7/2000  |

(Continued)

OTHER PUBLICATIONS

International Search Report and Written Opinion in International Application No. PCT/EP2014/059690, dated Jul. 29, 2014, 9 pages.

(Continued)

*Primary Examiner* — Kevin C Sirmons
*Assistant Examiner* — Tezita Z Watts
(74) *Attorney, Agent, or Firm* — Fish & Richardson P.C.

(57) ABSTRACT

A drive assembly for a drug delivery device is provided, including a piston rod which is moveable in a distal direction in order to deliver a dose of medication, and including a drive element which is configured to cause a movement of the piston rod. The drive assembly further includes a decelerating mechanism which is configured to decelerate the movement of the drive element such that the movement of the piston rod is decelerated during the dispense of a dose. The decelerating mechanism includes a decelerating element which is fixed with respect to a housing of the drug delivery device at least during the dispense of a dose and the drive element, wherein the drive element is configured to rotate with respect to the housing during the dispense of a (Continued)

dose, and wherein the decelerating element and the drive element rub against each other during the dispense of a dose.

17 Claims, 2 Drawing Sheets

(52) U.S. Cl.
CPC .... *A61M 5/31553* (2013.01); *A61M 5/31583* (2013.01); *A61M 5/31541* (2013.01); *A61M 5/482* (2013.01); *A61M 2005/2086* (2013.01); *A61M 2205/581* (2013.01)

(58) Field of Classification Search
CPC .............. A61M 5/31541; A61M 5/482; A61M 5/3155; A61M 5/31585; A61M 5/31576; A61M 2005/2086; A61M 2005/3143; A61M 2205/581; A61M 5/31501; A61M 2005/2026
See application file for complete search history.

(56) References Cited

U.S. PATENT DOCUMENTS

| | | | |
|---|---|---|---|
| 4,865,591 A | 9/1989 | Sams | |
| 5,092,842 A | 3/1992 | Bechtold et al. | |
| 5,226,895 A | 7/1993 | Harris | |
| 5,226,896 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,378,233 A | 1/1995 | Haber et al. | |
| 5,383,865 A | 1/1995 | Michel | |
| 5,391,157 A | 2/1995 | Harris et al. | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,807,346 A | 9/1998 | Frezza | |
| 5,820,602 A | 10/1998 | Kovelman et al. | |
| 5,851,079 A | 12/1998 | Horstman et al. | |
| 5,921,966 A | 7/1999 | Bendek et al. | |
| 5,957,896 A | 9/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,562,006 B1 | 5/2003 | Hjertman et al. | |
| 6,613,023 B2 | 9/2003 | Kirchhofer et al. | |
| 6,699,224 B2 | 3/2004 | Kirchhofer et al. | |
| 6,899,698 B2 | 5/2005 | Sams | |
| 6,932,794 B2 | 8/2005 | Giambattista et al. | |
| 6,936,032 B1 | 8/2005 | Bush, Jr. et al. | |
| 7,169,132 B2 | 1/2007 | Bendek et al. | |
| 7,241,278 B2 | 7/2007 | Moller | |
| 7,678,084 B2 | 3/2010 | Judson et al. | |
| 7,850,662 B2 | 12/2010 | Veasey et al. | |
| 8,186,233 B2 | 5/2012 | Joung et al. | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0097883 A1 | 5/2004 | Roe | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2007/0016143 A1 | 1/2007 | Miller et al. | |
| 2009/0275916 A1 | 11/2009 | Harms et al. | |
| 2011/0077595 A1* | 3/2011 | Eich | A61M 5/31501 604/135 |
| 2016/0067420 A1* | 3/2016 | Higgins | A61M 5/20 604/211 |

FOREIGN PATENT DOCUMENTS

| | | | |
|---|---|---|---|
| EP | 0937476 | A2 | 8/1990 |
| EP | 0496141 | A1 | 7/1992 |
| EP | 0897729 | A2 | 2/1999 |
| EP | 0937471 | A2 | 8/1999 |
| EP | 1776975 | A2 | 4/2007 |
| WO | 9307922 | A2 | 4/1993 |
| WO | 9324160 | A1 | 12/1993 |
| WO | 9938554 | A1 | 8/1999 |
| WO | 0110484 | A1 | 2/2001 |
| WO | 0230495 | A2 | 4/2002 |
| WO | 02092153 | A2 | 11/2002 |
| WO | 03080160 | A1 | 10/2003 |
| WO | 2006084876 | A1 | 8/2006 |
| WO | 2008053243 | A2 | 5/2008 |
| WO | 2009098502 | A2 | 8/2009 |
| WO | 2010066591 | A1 | 6/2010 |
| WO | WO 2012/084720 | | 6/2012 |

OTHER PUBLICATIONS

International Preliminary Report on Patentability in International Application No. PCT/EP2014/059690, dated Dec. 1, 2015, 7 pages.
"Pen-injectors for medical use—Part 1: Pen-injectors—Requirements and test methods," International Standard, reference No. ISO 11608-1:2000(E), first edition Dec. 15, 2000, 32 pages.
Rote Liste, "50. Hypophysen-, Hypothalamushormone, andere regulatorische Peptide u. ihre Hemmstoffe," Chapter 50 ed. 2008, 20 pages.

\* cited by examiner

DRIVE ASSEMBLY FOR A DRUG DELIVERY AND DRUG DELIVERY DEVICE

CROSS REFERENCE TO RELATED APPLICATIONS

The present application is a U.S. National Phase Application pursuant to 35 U.S.C. § 371 of International Application No. PCT/EP2014/059690 filed May 13, 2014, which claims priority to European Patent Application No. 13169309.5 filed May 27, 2013. The entire disclosure contents of these applications are herewith incorporated by reference into the present application.

FIELD OF INVENTION

The present disclosure relates to a drive assembly for a drug delivery device. In particular, the disclosure relates to pen-type drug delivery devices.

BACKGROUND

Pen-type drug delivery devices are used for injections by persons without formal medical training. This is increasingly common for self-treatment among patients having diabetes or the like. Such self-treatment enables patients to effectively manage their disease. Pen-type drug delivery devices usually comprise a housing in which a drive mechanism is located. Some kinds of drug delivery devices also comprise a compartment to accommodate a cartridge in which the drug is contained. By means of the drive mechanism, a piston in the cartridge is displaced such that the drug accommodated therein is dispensed through a needle.

Prior to injection, the required dose of a drug is set by means of a dose setting mechanism. Common designs of dose setting mechanisms comprise a number of tubular or sleeve-like elements such as a dose dial sleeve, a dose indicating sleeve, a drive sleeve or a ratchet sleeve. Such sleeves are often accommodated within and connected to each other.

Some devices may comprise a brake mechanism in order to allow a user to control the dispensing speed of a drug delivery device. Thereby, the injection of a drug may be more comfortable for a user.

Document WO 2008/053243 describes a user actuable brake for allowing a user to control a rate of delivery of medicine.

Document U.S. Pat. No. 4,333,359 describes a braking member for the control of an injection procedure.

SUMMARY

It is an object of the present invention to provide a drive assembly for a drug delivery device having improved properties.

According to one aspect of the invention, a drive assembly for a drug delivery device is provided, comprising a piston rod which is moveable in a distal direction in order to deliver a dose of a drug, and comprising a drive element which is configured to cause a movement of the piston rod in a distal direction. The drive assembly further comprises a decelerating mechanism which is configured to decelerate the movement of the drive element such that the movement of the piston rod in a distal direction is decelerated during the injection of a dose. The decelerating mechanism comprises a decelerating element which is fixed with respect to a housing of the drug delivery device at least during the dispense of a dose and the drive element, wherein the drive element is configured to rotate with respect to the housing during the dispense of a dose and wherein the decelerating element and the drive element rub against each other during the dispense of a dose. In particular, a rotation of the drive element is decelerated by means of the decelerating mechanism. In one embodiment, the decelerating element may be fixed with respect to a guiding element. The guiding element may be fixed with respect to the housing or may be comprised by the housing.

The advantage of a decelerating mechanism which is configured to decelerate the movement of the drive element such that the movement of the piston rod in a distal direction is decelerated during a dispensing of a dose is that a user may control the dispensing speed. Furthermore, elastic energy which is stored in the drive assembly, for example in the mechanics or in the piston, may have enough time to transfer into a movement of the piston. Thereby, the dosing accuracy may be increased.

According to one embodiment, the decelerating element may comprise a first contact surface and the drive element comprises a second contact surface. During the setting of a dose, the first contact surface and the second contact surface may be arranged with a distance to each other. During the dispense of a dose, the first contact surface and the second contact surface may be in contact with each other, in particular, the first and the second contact surface may rub against each other during the dispense of a dose.

The first contact surface and the second contact surface may be roughened with respect to a circumjacent surface. According to one embodiment, a coating may be applied to at least one of the first and the second contact surface.

The first contact surface of the decelerating element may be faced in a radial inward direction. For example, the first contact surface may be arranged at an inner circumference of the housing. Alternatively, the first contact surface may be faced towards a proximal end of the device. The proximal end of the drug delivery device may be an end which is furthest away from a dispensing end of the device.

According to one embodiment, the drive assembly comprises a guiding element. The guiding element may be, for example, a thread nut. The guiding element may be fixed with respect to the housing. Furthermore, the guiding element is in threaded engagement with the piston rod. When the piston rod is rotated, for example, due to a rotation of the drive element, the piston rod is caused to axially move as a result of its cooperation with the guiding element. In particular, the piston rod is rotated by the drive element during the setting of a dose such that it is moved in a distal direction. Thereby, a dose may be dispensed from the drug delivery device. The distal direction may be a direction towards a dispensing end of the device.

The advantage of a drive assembly wherein an axial movement of the piston rod in a distal direction may be caused by a rotational movement of a drive element is that no considerably great axial movement of any component of the drive assembly is required.

The first contact surface may be located at a surface of the guiding element, in particular at a surface which is faced towards a proximal end of the device. In particular, the first contact surface may be arranged at a surface of the guiding element which is faced towards the drive element. The first contact surface may at least partially cover the surface of the guiding element which is faced towards a proximal end of the device.

According to one embodiment, the decelerating element may be an integral part of another component of the drive assembly. For example, the decelerating element may be in integral part of the housing. In particular, the decelerating element may be located at an inner circumference of the housing. Alternatively, the decelerating element may be an integral part of the guiding element.

The second contact surface of the drive element may be faced in a radial outward direction with respect to a longitudinal axis of the drive assembly. For example, the second contact surface may be arranged at an outer circumference of the drive element. Alternatively, the second contact surface of the drive element may be faced towards a dispensing end of the device. In particular, the second contact surface may at least partially cover the surface of the drive element which is directed towards a dispensing end of the device.

The first and the second contact surface may be configured such that they may be in contact with each other throughout a whole dispense operation. Thereby, a movement of the piston rod may be decelerated at any time during a dispense operation. Alternatively, the first and the second contact surface may be configured such that they are in contact only during a period of a dispense operation. Thereby, a user may control the speed of a dispense operation.

According to one embodiment, the drive assembly comprises an actuator. The actuator may be configured as a button. The actuator may be depressed by a user in order to dispense a dose of a drug. In order to dispense a dose, the actuator may be fully depressed or partially depressed by a user. According to one embodiment, the more the actuator is depressed, the more the dispensing speed may be decelerated. Alternatively, the more the actuator is depressed, the less the dispensing speed, respectively the drive element, may be decelerated. For example, the first and the second contact surface are pressed together when a user depresses the actuator. The more a user depresses the actuator, the higher is the force with which the decelerating element and the drive element, in particular the first and the second contact surface are pressed together. Alternatively, the more a user depresses the actuator, the less are the decelerating element and the drive element in contact with each other. In particular, the more a user depresses the actuator, the less are the first and the second contact surface in contact with each other. This has the advantage that a friction force which decelerates the movement of the piston rod may be influenced by a user. In particular, a user may decide weather the dispensing speed should be slow or fast.

The drive element may be engaged with the piston rod. For example, the drive element may comprise splines, which are engaged with corresponding grooves of the piston rod. The grooves may extend along the entire length of the piston rod. In particular, the drive element may be axially moveable with respect to the piston rod. Furthermore, the drive element may be rotationally fixed with respect to the piston rod.

According to a preferred embodiment, the drive assembly is configured such that a rotation of the drive element causes a rotational movement of the piston rod. In particular, a rotation of the drive element causes a combined axial and rotational movement of the piston rod. In particular, when the piston rod is rotated by the drive element, the piston rod rotates through the guiding element. During the setting of a dose, the drive element may be fixed with respect to the housing.

According to one embodiment, the drive assembly may comprise a locking member. The locking member may be fixed with respect to the housing during the setting of a dose. In particular, the locking member and the housing may comprise corresponding engagement means. The corresponding engagement means may be engaged during the setting of a dose. The drive element may be fixedly coupled to the locking member such that the drive member may be fixed with respect to the housing by means of the locking member at least during the setting of a dose. The drive element and the locking member may be fixed with respect to each other such that the movement of the locking member causes a corresponding movement of the drive element.

During the dispensing of a dose, the locking member may rotate with respect to the housing. Thereby, the drive element may rotate with respect to the housing during the dispensing of a dose. Thereby, the drive element may effect a movement of the piston rod. In order to enable a rotation of the locking member, the locking member has to be released from its engagement with the housing. For example, the locking member has to be axially moved with respect to the housing in order to enable a rotation of the locking member. For example, the locking member may be moved in a distal direction in order to enable a rotation of the locking member.

The drive assembly may comprise a rotation member. The rotation member may be rotated during the setting and during the dispensing of a dose. During the setting of a dose, the rotation member may be rotated in a dose setting direction, for example in a clockwise direction. During the dispensing of a dose, the rotation member may be rotated in a dose dispensing direction, for example an anticlockwise direction. The rotation member may be coupled to the locking member. When the actuator is actuated, the rotation member may move the locking member out of its engagement with the housing. Furthermore, a rotation of the rotation member may cause a rotation of the locking member during the dispensing of a dose.

The rotation member may comprise a ratchet mechanism. The ratchet mechanism may comprise a ratchet arm. The rotation member may be coupled with respect to the locking member by means of the ratchet mechanism. The ratchet mechanism may allow a rotation of the rotation member in a dose setting direction with respect to the locking member. An unintended rotation of the rotation member in a dose dispensing direction may be inhibited during the setting of a dose by means of the ratchet mechanism.

The assembly may comprise a dose setting member which is configured to be rotated in a dose setting direction in order to set a dose. The rotation member may be rotated when a user rotates the dose setting member.

According to one embodiment, the drive assembly comprises a spring member. The spring member may be a torsion spring. The spring member may be loaded during the setting of a dose. When the actuator is operated by a user, energy may be released from the spring member. The energy which is released from the spring member may cause the drive element to rotate. In particular, the spring member may cause the rotation member to rotate. One end of the spring member may be fixedly coupled to the housing or to another part which is fixed with respect to the housing. The other end of the spring member may be fixedly coupled to the rotation member. When the rotation member is rotated in a dose setting direction, the spring member may be wound up. Thereby, energy may be stored in the spring member.

Furthermore, a drug delivery device is provided, the drug delivery device comprising a drive assembly. The drive assembly may be configured as previously described.

The drug delivery device may be an injection device, in particular a pen-type device. The drug delivery device may be suited to deliver a dose of a drug to a user. A dose may be delivered by depressing the actuator. The drug delivery device may be a variable dose device such that a user can select the size of a dose. In particular, a user may select the size of a dose by rotating the dose setting member. The drug delivery device may be configured for multiple dose applications. The drug may be delivered to a user by means of a needle. The device may be delivered to a user in a fully assembled condition ready for use. In particular, the device may be prefilled. The drug delivery device may be a disposable device. The term "disposable" means that the drug delivery device cannot be reused after an available amount of a drug has been delivered from the drug delivery device. Alternatively, the drug delivery device may be a reusable device. The drug delivery device may be configured to deliver a liquid drug. The drug may be, for example, insulin.

The term "drug", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu- Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4 (1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Further features, refinements and expediencies become apparent from the following description of the exemplary embodiments in connection with the figures.

Figure 1:
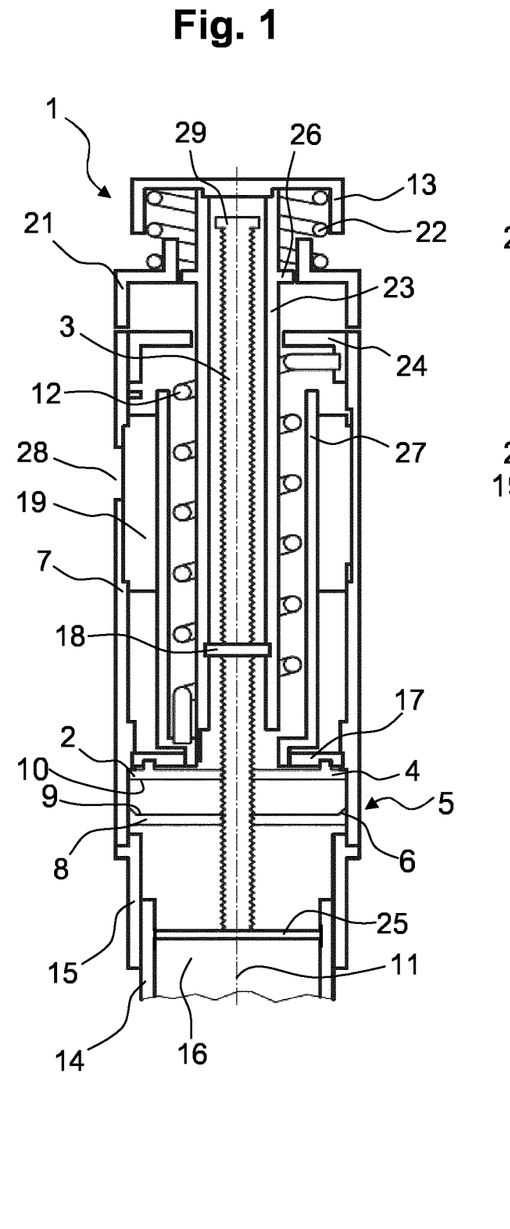
FIG. 1 shows a drug delivery device comprising a decelerating element in a state when the actuator is not actuated.

FIG. 1 shows a drug delivery device 1 comprising an assembly 2. In particular, FIG. 1 shows the drug delivery device 1 in a state when it is not being operated, i.e. when no dose is being delivered from the device.

DETAILED DESCRIPTION

The drive assembly 2 comprises a piston rod 3, which is configured to be moved in a distal direction in order to dispense a dose. In particular, the piston rod 3 is configured to move a piston 16 which is arranged in a cartridge 14 towards the dispensing end of the drug delivery device 1. In particular, the piston rod 3 comprises a bearing 25, wherein the bearing 25 is in contact with the piston 16. The cartridge is arranged in a cartridge holder 15, which is connected to a housing 7. The piston rod 3 is configured as a lead screw.

In order to set a dose, the drive assembly 2 comprises a dose setting member 21. The dose setting member 21 may be rotated by a user. In particular, the dose setting member 21 is axially fixed, but rotationally moveable with respect to the housing 7. In particular, the length of the drug delivery device 1 does not change during a rotation of the dose setting member 21. The drive assembly further comprises a drive shaft 23. By rotating the dose setting member 21, the drive shaft 23 is also rotated. In particular, the drive shaft 23 may be rotationally fixed with respect to the dose setting member 21 during the setting of a dose by means of splines 26. The splines 26 may engage in corresponding grooves (not shown) of the dose setting member 21. The drive assembly 2 furthermore comprises a rotation member 27. The rotation member 27 is configured as a sleeve. The rotation member 27 is arranged concentrically around the drive shaft 23. The rotation member 27 may be fixed to the drive shaft 23 by a snap connection. The rotation member 27 is axially fixed with respect to the drive shaft 23. For assembly reasons, the drive shaft 23 and the rotation member 27 are designed as separate parts. In an alternative embodiment, the drive shaft 23 and the rotation member 27 may be designed as one part. Rotating the drive shaft 23 in a dose setting direction also rotates the rotation member 27. The dose setting direction may be a clockwise direction.

The drive assembly 2 comprises a spring member 12. The spring member 12 may be a torsion spring. One end of the spring member 12 is fixed to a zero stop 24, which will be described later. In an alternative embodiment, one end of the spring member 12 may be fixed to the housing 7. The other end of the spring member 12 is fixed to the rotation member 27. When the rotation member 27 is rotated during the setting of a dose, the spring member 12 is wound up, such that energy is stored in the spring member 12.

The drive assembly 2 further comprises an indicator 19. The indicator 19 may be, for example, a number sleeve. The indicator 19 is configured to indicate the amount of a set dose to a user. For example, the amount of a set dose may be shown through a window 28 in the housing 7 of the drug delivery device 1. The indicator 19 is rotationally fixed, but axially moveable with respect to the rotation member 27. For example, the indicator 19 may comprise splines at its inner circumference which may engage in corresponding grooves of the rotation member 27. In particular, the indicator 19 is arranged concentrically around the rotation member 27. Furthermore, the indicator 19 is in threaded engagement with the housing 7. During the setting of a dose, the indicator 19 is rotated by the rotation member 27 in the dose setting direction. Thereby, the indicator 19 is forced to move in a distal direction because of its threaded engagement with the housing 7. In order to cancel a set dose, the dose setting member 21 may be rotated in a dose cancelling direction. The dose cancelling direction may be the anti-clockwise direction.

The drive assembly 2 further comprises a locking member 17. The locking member 17 is rotationally fixed with respect to the housing 7 during the setting of a dose. For example, the locking member 17 comprises splines which engage with corresponding grooves of the housing 7. On an inner circumference of the locking member 17, a set of teeth (not shown) is arranged. The rotation member 27 is engaged with the set of teeth of the locking member 17 by means of at least one ratchet arm (not shown). In particular, the locking member 17 and the rotation member 27 are engaged such that the rotation of the rotation member 27 in a dose setting direction is allowed during the setting of a dose, and an unintended rotation of the rotation member 27 in a dose cancelling direction is inhibited. Thereby, it is inhibited that the torque from the spring member 12 rotates the rotation member 27 in a dose cancelling direction when a user releases the dose setting member 21. During the setting of a dose, the at least one ratchet arm of the rotation member 27 is moved over the teeth of the locking member 17. Thereby, an audible click may be produced with each unit set.

In order to cancel a set dose, a user rotates dose setting member 21 in a dose cancelling direction. During the cancelling of a dose, the drive shaft 23 may rotate relative to the rotation member 27 for a small amount compressing the biasing arm. Thereby, a feature, for example a protrusion of the drive shaft 23, slides over the at least one ratchet arm of the rotation member 27. Thereby, the at least one ratchet arm of the rotation member 27 is pressed in radial inward direction. Thereby, the engagement between the rotation member 27 and the locking member 17 is temporarily released, such that the rotation member 27 may be rotated in a dose cancelling direction.

A last dose member 18 is arranged between the piston rod 3 and the drive shaft 23. The last dose member 18 may be a last dose nut. The last dose member 18 is in threaded engagement with the piston rod 3. Furthermore, the last dose member 18 is engaged with the drive shaft 23 by means of external ribs which engage in corresponding grooves inside the drive shaft 23. In particular, the last dose member 18 is rotationally fixed but axially moveable with respect to the drive shaft 23. When the drive shaft 23 rotates, for example during the setting of a dose, the last dose member 18 is rotated by the drive shaft 23. Thereby, the last dose member 18 moves along the piston rod. When a last dose is selected, the last dose member 18 abuts a stop feature 29. The stop feature 29 is arranged at a proximal end of the piston rod 3. When the last dose member 18 abuts the stop feature 29, the further setting of a dose is inhibited. In particular, the last dose member 18 inhibits the setting of a dose which exceeds the amount of remaining drug in the cartridge 14.

Figure 2:
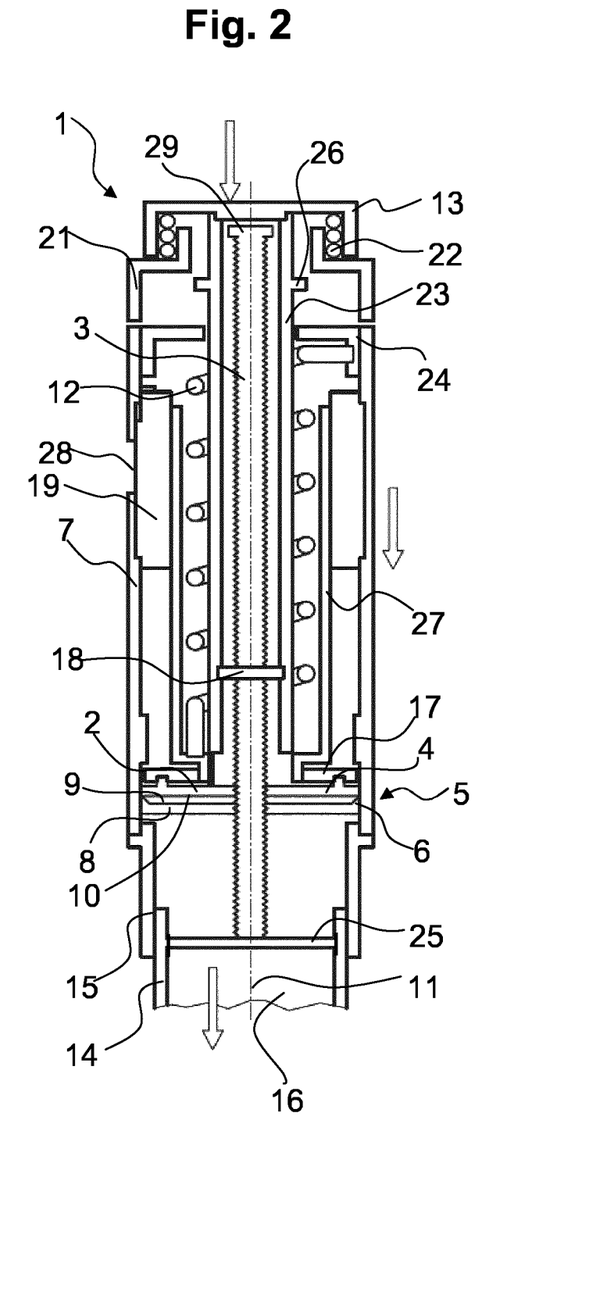
FIG. 2 shows the drug delivery device of FIG. 1 in a state when the actuator is actuated by a user.

In order to dispense a dose, the actuator 13 has to be actuated by a user. FIG. 2 shows the drug delivery device 1 in a state when the actuator 13 is actuated.

When the actuator 13 is actuated, in particular moved in a distal direction, the drive shaft 23 is also moved in a distal direction. Thereby, the drive shaft 23 is disengaged from the dose setting member 21. When the drive shaft 23 is moved in a distal direction, the rotation member 27 and the locking member 17 are also moved in a distal direction together with the drive shaft 23. Thereby, the locking member 17 is disengaged from its engagement with the housing 7. In particular, the locking member 17 is allowed to rotate with respect to the housing 7 when the actuator 13 is actuated by a user. When the locking member 17 is enabled to rotate with respect to the housing 7, the energy which is stored in the spring member 12 may be released. In particular, the spring member 12 exerts a torque on the rotation member 27, such that the rotation member 27 is rotated during the dispensing of a dose. A rotation of the rotation member 27 during the dispensing of a dose also rotates the locking member 17.

The drive assembly 2 comprises a drive element 4. The drive element 4 is configured as a spline nut. The drive element 4 is connected to the locking member 17. In particular, the drive element 4 is rotationally and axially fixed with respect to the locking member 17. Thereby, the drive element 4 rotates during the dispensing of a dose. Furthermore, the drive element 4 is engaged with the piston rod 3. In particular, the drive element 4 comprises splines, which are engaged with axial grooves of the piston rod 3. Thereby, the drive element 4 is rotationally fixed but axially moveable with respect to the piston rod 3.

The drive element 4 may comprise a feedback feature (not shown). For example, at the outer circumference of the drive element 4, at least one, for example two, clicker arms, may be arranged. When the drive element 4 rotates during the dispensing of a dose, the clicker arms may move over teeth in the housing 7, thereby creating an audible feedback. The feedback may indicate to a user that a dose is currently dispensed. Accordingly, an end of the audible feedback indicates to a user that a complete dose has been dispensed.

The drive assembly 2 further comprises a guiding element 8. The guiding element 8 is configured as a thread nut. The guiding element 8 is in threaded engagement with the piston rod 3. The guiding element 8 is fixed with respect to the housing 7 of the drug delivery device 1. When the drive element 4 rotates during the dispensing of a dose, the piston rod 3 is also rotated. Due to the threaded engagement between the piston rod 3 and the guiding element 8, the rotation of the piston rod 3 causes the piston rod 3 to move in a distal direction. Thereby, the piston 16 is moved in a distal direction and thereby a dose is dispensed. During the dispensing of a dose, the indicator 19 is rotated back to its initial position. In particular, during the dispensing of a dose, the indicator 19 performs a combined rotational and axial movement towards a proximal end of the device, until the indicator 19 abuts a zero stop 24. The zero stop 24 is rigidly fixed to the housing 7. Alternatively, the zero stop 24 may be an integral part of the housing 7. When the indicator 19 abuts the zero stop 24, a further rotation of the rotation member 27 in a dose dispensing direction due to the torque of the spring member 12 is inhibited. Thereby, the further dispense of a dose is inhibited.

When a user releases the actuator 13, a reset spring 22, which is arranged between the actuator and the dose setting member 21, moves the actuator back to its initial position. Thereby, the drive shaft 23 is moved in a proximal direction together with the actuator 13. Thereby, the drive shaft 23 reengages with the dose setting member 21. Furthermore, the locking member 17 reengages with the housing 7.

The drive assembly 2 further comprises a decelerating mechanism 5, which is configured to decelerate the movement of the drive element 4 during the dispensing of a dose. Thereby, the movement of the piston rod 3 in a distal direction is decelerated. By means of the decelerating mechanism 5, a user may control the speed of a dispense operation. Thereby, an injection may be more comfortable for a user. For example, the more the actuator 13 is depressed by a user, the more a movement of the piston rod 3 is decelerated. Such an embodiment is described in the following in accordance with FIGS. 1 and 2. In a further embodiment, the more the actuator 13 is depressed by a user, the less a movement of the piston rod 3 is decelerated. Such an embodiment is described in accordance with FIGS. 3 and 4. In the embodiment shown in FIGS. 1 and 2 the contact surface 9 of decelerating element is arranged at the guiding element 8. In another embodiment shown in FIGS. 3 and 4 the contact surface 9 is arranged at the housing 7.

A first embodiment of the decelerating mechanism 5 is shown in FIGS. 1 and 2. The decelerating mechanism 5 comprises a decelerating element 6 which is fixed with respect to the housing 7, in particular to the guiding element 8 of the assembly 2. In the embodiment shown in FIGS. 1 and 2, the decelerating element 6 is comprised by the guiding element 8. Furthermore, the decelerating mechanism 5 comprises the drive element 4. The decelerating element 6 comprises a first contact surface 9. The first contact surface 9 is configured as a roughened surface area on the guiding element 8. For example, the decelerating element 6 may be a coating on the guiding element 8. The first contact surface 9 extends over a part of the surface of the guiding element 8 which is faced towards a proximal end of the device. In particular, the first contact surface 9 is faced towards the drive element. Furthermore, the drive element 4 comprises a second contact surface 10. The second contact surface is configured as a roughened surface area on the drive element 4. For example, the second contact surface 10 may comprise a coating. In FIGS. 1 and 2, the decelerating element 6 is indicated by a triangular protrusion on the guiding element 8 for visualisation. However, the triangular protrusion is not a structural element of the guiding element 8. It only serves to indicate the position of the decelerating element 6.

During the dispensing of a dose, the drive element 4 is in contact with the decelerating element 6, as for example shown in FIG. 2. In particular, the drive element 4 is in contact with the guiding element 8. In FIG. 2, a small gap is shown between the drive element 4 and the guiding element 8 for clarity reasons. In practice, the drive element 4 and the guiding element 8 may be in contact such that no gap occurs. When the drive element 4 is rotated during the dispensing of a dose, the drive element 4 and the decelerating element 6 rub against each other. Thereby, a rotation of the drive element 4 is decelerated. In particular, the velocity of the rotation of the drive element 4 is decelerated. Since the drive element 4 is rotationally fixed with respect to the piston rod 3, the rotation of the piston rod 3 is also decelerated. Thereby, the decelerating mechanism 5 decelerates a movement of the piston rod 3 in a distal direction during the dispensing of a dose.

At the end of the dispensing operation, the spring force from the spring member 12 decreases, and the influence of the decelerating mechanism 5 increases. Thereby, an elastic energy which is stored in the drive assembly 2, for example in the piston 16 or in other components of the assembly, has time to transfer into a movement of the piston 16. Thereby, the dose accuracy is increased. In particular, the hold time a user needs to depress the actuator 13 after the end of the audible feedback until a complete dose has been dispensed is reduced.

Figure 3:
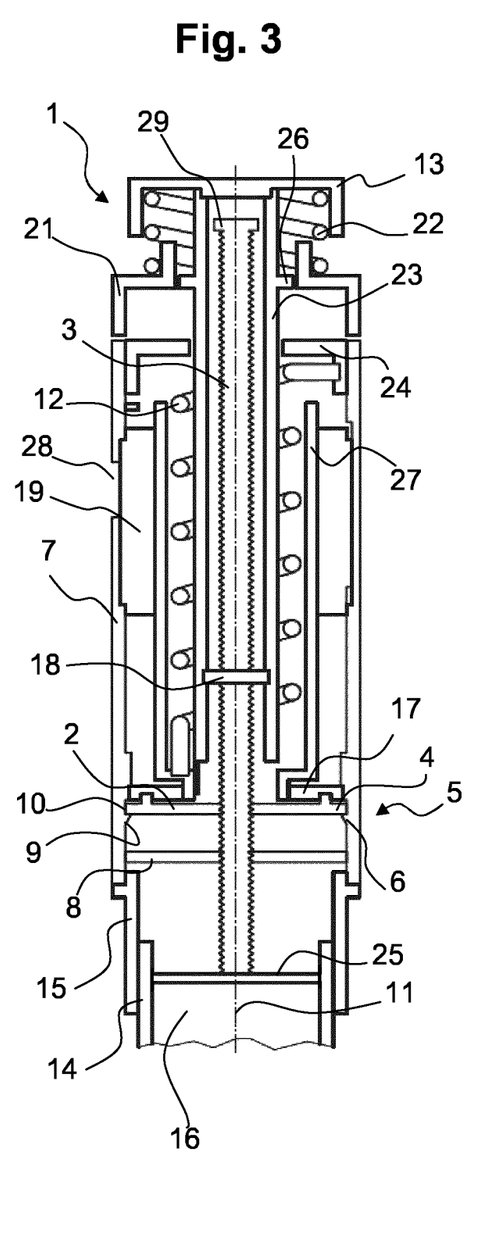
FIG. 3 shows a further embodiment of a drug delivery device comprising a decelerating element in a state when the actuator is not actuated.
Figure 4:
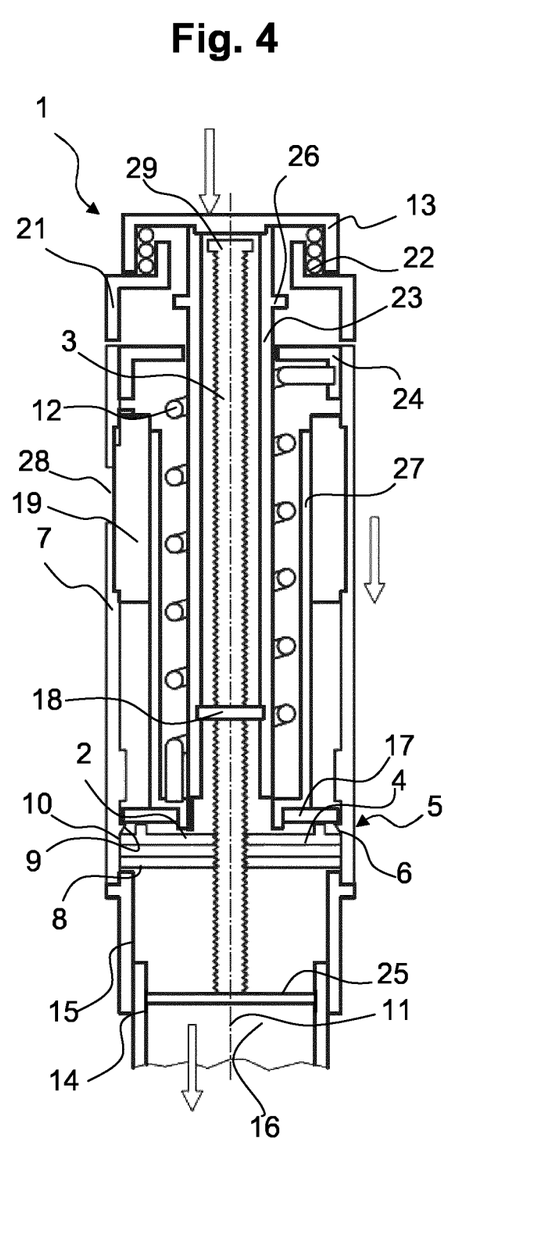
FIG. 4 shows the drug delivery device of FIG. 3 in a state when the actuator is actuated.

FIGS. 3 and 4 show a further embodiment of a drug delivery device 1 comprising a drive assembly 2. The drive assembly 2 comprises a further embodiment of a decelerating mechanism 5. FIG. 3 shows the drug delivery device in a state when the device it is not operated. FIG. 4 shows the drug delivery device in a state when the actuator 13 is actuated. Apart from the different configuration of the decelerating mechanism 6, the functionality of the drug delivery device 1 is the same as described in accordance with FIGS. 1 and 2.

In the embodiment shown in FIGS. 3 and 4, the decelerating element 6 comprises a first contact surface 9. The first contact surface is located at the housing 7, in particular at an inner circumference of the housing 7. In particular, the first contact surface 9 is configured as a roughened surface on the housing 7. For example, the decelerating element 6, in particular the first contact surface 9 comprises a coating on the housing 7.

In FIGS. 3 and 4, the decelerating element 6 is indicated by a triangular protrusion on the housing 7 for visualisation. However, the triangular protrusion is not a structural element of the housing. It only serves to indicate the possible position of the decelerating element 6.

The decelerating mechanism 5 further comprises the drive element 4. The drive element 4 comprises a second contact surface 10. The second contact surface 10 is located at the outer circumference of the drive element 4. In particular, the drive element 4 comprises a coating or a roughened surface at its outer circumference.

When the drug delivery device 1 is in a non-operation state, as shown in FIG. 3, the decelerating element 6 and the drive element 4 are not in contact with each other. In particular, the first contact surface 9 and the second contact surface 10 are not in contact with each other.

When the actuator 13 is depressed by a user in order to dispense a dose of a drug, the drive element 4 is moved in a distal direction. Thereby, the drive element 4 contacts the decelerating element 6. Thereby, the rotation of the drive element 4 and a movement of the piston rod 3 are decelerated, as already described in accordance with FIGS. 1 and 2.

According to one embodiment, the extension of the decelerating element 6, in particular of the first contact surface 9, along a longitudinal axis 11 of the assembly 2 may be such that the drive element 4, in particular the outer circumference of the drive element 4, is always in contact with the decelerating element 6 during the dispense of a dose. Thereby, the movement of the piston rod 3 is always decelerated during the dispensing of a dose.

In a further embodiment, the extension and location of the decelerating element 6, in particular of the first contact surface 9, may be such that the drive element 4 is only in contact with the decelerating element 6 when the actuator 13 is depressed to a certain amount. For example, the drive element 4 may be in contact with the decelerating element 6 when the actuator 13 is not fully depressed, for example half depressed. When the actuator 13 is fully depressed, the drive element 4 may be moved beyond the first contact surface 9, such that the rotation of the drive element 4 is not decelerated when the actuator 13 is fully depressed. Thereby, a user may control the speed of a dispense operation. In particular, the more the actuator 13 is depressed by a user, the less a movement of the piston rod 3 is decelerated.

In FIG. 4, the drug delivery device 1 is shown in a state when the actuator 13 is fully depressed. Thereby, the drive element 4 has been moved beyond the decelerating element 6. In particular, the drive element 4 is arranged in front of the decelerating element 6, seen from the dispensing end of the device. Thereby, the drive element 4 and the decelerating element 6 are not in contact anymore. Consequently, the movement of the piston rod 3 is not decelerated anymore.

The invention claimed is:

1. A drive assembly for a drug delivery device, the drive assembly comprising:
    a piston rod which is moveable in a distal direction along a longitudinal axis of the drive assembly to deliver a dose of medication;
    an actuator which is configured to be depressed in order to deliver the dose of medication;
    a drive element which is configured to cause a movement of the piston rod in the distal direction;
    a guiding element which is in threaded engagement with the piston rod; and
    a decelerating mechanism which is configured to decelerate a movement of the drive element such that the movement of the piston rod in the distal direction is decelerated during dispense of the dose of medication,
    wherein the decelerating mechanism comprises a decelerating element which is fixed with respect to a housing of the drug delivery device at least during the dispense of the dose of the medication and the drive element,
    wherein the drive element is configured to rotate with respect to the housing during the dispense of the dose of medication,
    wherein the decelerating element and the drive element are configured to rub against each other during the dispense of the dose of medication,
    wherein the decelerating element comprises a first contact surface and the drive element comprises a second contact surface, and
    wherein the first contact surface at least partially covers a surface of the guiding element facing towards a proximal end of the drive assembly, and the second contact surface at least partially covers a surface of the drive element directed towards a dispensing end of the drive assembly, wherein the first contact surface and the second contact surface are arranged with a distance to each other during a setting of the dose of medication, and wherein the first contact surface and the second contact surface are configured to rub against each other during the dispense of the dose of medication.

2. The drive assembly according to claim 1, wherein a rotation of the drive element causes a combined axial and rotational movement of the piston rod.

3. The drive assembly according to claim 1, wherein the guiding element is configured such that the piston rod is caused to axially move in the distal direction when the drive element rotates the piston rod.

4. The drive assembly according to claim 1, wherein the drive element is engaged with the piston rod.

5. The drive assembly according to claim 1, wherein the drive element is axially moveable with respect to the piston rod.

6. The drive assembly according to claim 1, wherein the drive element is rotationally fixed with respect to the piston rod.

7. The drive assembly according to claim 1, wherein the drive element is fixed with respect to the housing during the setting of the dose.

8. The drive assembly according to claim 1, wherein the second contact surface is faced in a radial outward direction with respect to the longitudinal axis of the drug delivery device.

9. The drive assembly according to claim 1, wherein the decelerating element is an integral part of the housing of the drug delivery device.

10. The drive assembly according to claim 1, wherein the first contact surface and the second contact surface are configured to at least partially overlap during the dispense of the dose, and wherein a degree of overlap of the first contact surface and the second contact surface depends on a grade of depression of the actuator.

11. The drive assembly according to claim 3, wherein the decelerating element is an integral part of the guiding element.

12. The drive assembly according to claim 1, wherein the first contact surface is configured as a roughened surface area on a guiding element and the second contact surface is configured as a roughened surface area on the drive element.

13. The drive assembly according to claim 1, comprising a spring member, wherein energy is released from the spring member when the actuator is operated by a user, and wherein the energy which is released from the spring member causes the drive element to rotate.

14. The drive assembly according to claim 1, wherein the drive assembly is configured such that the more the actuator is depressed, the more the drive element is decelerated, wherein the more a user depresses the actuator, the higher is the force with which the decelerating element and the drive element are pressed together.

15. The drive assembly according to claim 1, wherein the drive assembly is configured such that the more the actuator is depressed, the less the drive element is decelerated, wherein the more a user depresses the actuator, the less the decelerating element and the drive element are in contact with each other.

16. The drive assembly according to claim 1, wherein the surface of the guiding element faces toward the drive element.

17. The drive assembly according to claim 1, wherein the first contact surface and the second contact surface are configured to contact each other throughout an entirety of a dispense operation.

* * * * *

UNITED STATES PATENT AND TRADEMARK OFFICE
CERTIFICATE OF CORRECTION

| | | |
|---|---|---|
| PATENT NO. | : 10,543,320 B2 | Page 1 of 1 |
| APPLICATION NO. | : 14/894179 | |
| DATED | : January 28, 2020 | |
| INVENTOR(S) | : Andreas Bernert | |

It is certified that error appears in the above-identified patent and that said Letters Patent is hereby corrected as shown below:

On the Title Page

Item (54) and in the Specification, Column 1, Line 1, (Title), after "DELIVERY" insert -- DEVICE --

Signed and Sealed this
Fifth Day of May, 2020

Andrei Iancu
*Director of the United States Patent and Trademark Office*